(12) United States Patent
Lewandowski et al.

(10) Patent No.: US 8,945,664 B1
(45) Date of Patent: Feb. 3, 2015

(54) MECHANICAL STABILITY OF THE BIOMIMETIC COATING BY CROSS LINKING OF SURFACTANT POLYMER

(75) Inventors: Jan J. Lewandowski, South Euclid, OH (US); Yubiao Liu, Solon, OH (US)

(73) Assignee: Greatbatch Ltd., Clarence, NY (US)

( * ) Notice: Subject to any disclaimer, the term of this patent is extended or adjusted under 35 U.S.C. 154(b) by 360 days.

(21) Appl. No.: 13/283,763

(22) Filed: Oct. 28, 2011

Related U.S. Application Data

(60) Provisional application No. 61/408,183, filed on Oct. 29, 2010.

(51) Int. Cl.
*B05D 3/00* (2006.01)
*C08L 5/02* (2006.01)
*C08G 63/91* (2006.01)

(52) U.S. Cl.
USPC .............. 427/2.24; 427/2.1; 524/52; 525/54.2

(58) Field of Classification Search
CPC ........................ A61L 33/0017; A61L 33/00
See application file for complete search history.

(56) References Cited

U.S. PATENT DOCUMENTS

| 5,914,182 | A | * | 6/1999 | Drumheller | ................. | 428/308.4 |
| 5,916,585 | A | * | 6/1999 | Cook et al. | .................... | 424/426 |
| 6,309,660 | B1 | | 10/2001 | Hsu et al. | | |
| 7,276,474 | B2 | * | 10/2007 | Marchant et al. | ............ | 514/14.9 |
| 7,303,814 | B2 | | 12/2007 | Lamberti et al. | | |
| 2010/0069608 | A1 | | 3/2010 | Lloyd et al. | | |
| 2010/0256292 | A1 | | 10/2010 | Jakob et al. | | |

OTHER PUBLICATIONS

Kim et al. Swelling behavior and mechanical strength of crosslinked dextran hydrogel. Macromolecular Research vol. 11, No. 4. pp. 291-295. 2003.*

Kim et al., Swelling Behavior and Mechanical Strength of Crosslinked Dextran Hydrogel, (Macromolecular Research, vol. 11, No. 4), pp. 291-295, (2003), Chonnam National University, Gwangju, Korea.

Hoffmann et al., Characterisation of a new bioadhesive system based on polysaccharides with the potential to be used as bone glue, (Springer Science+Business Media, LLC (2009).

Cremers et al., Biodegradable ion-exchange microspheres based on modified polylysines, (Journal of Controlled Release 36 (1995).

* cited by examiner

*Primary Examiner* — Cachet Sellman
(74) *Attorney, Agent, or Firm* — Steven W. Winn

(57) ABSTRACT

A biomimetic surfactant polymer modified with various crosslinking embodiments is described. The crosslinking embodiments provide a biomimetic surfactant coating that is designed to resist cracking, scratching, spalling and chemical dissolution. The crosslinking embodiments comprise the use of various hydrophilic and hydrophobic functional groups. The modified biomimetic surfactant adheres to different substrate surfaces, particularly the surfaces of medical devices.

29 Claims, 9 Drawing Sheets

MECHANICAL STABILITY OF THE BIOMIMETIC COATING BY CROSS LINKING OF SURFACTANT POLYMER

CROSS-REFERENCE TO RELATED APPLICATION

The present application claims priority from U.S. Provisional Application Ser. No. 61/408,183 filed Oct. 29, 2010.

BACKGROUND OF THE INVENTION

1. Field of the Invention

The present invention is related generally to biocompatible coatings. More specifically, the present invention is related to a modification of the chemical structure of the biocompatible coating to increase its mechanical stability on a surface of a substrate.

2. Background Art

Implantable medical devices including, pacemakers, defibrillators, neurostimulators, venous introducers, and catheters are devices that are well known to help improve health and sustain life. However, despite the significant benefits that implantable medical devices provide, their use could lead to thrombosis, a serious medical problem that could result in death. Thrombosis is the formation of a blood clot within a blood vessel that obstructs blood flow leading to possible stroke, heart attack, organ failure and death.

Medical device related thrombosis initially occurs as a result of an interaction between blood and the surface of the medical device when they are in contact with each other. Once blood is in contact with the medical device, blood platelets and other blood constituents begin to coagulate and clot on the device surface. Blood clotting is known to occur on both metallic and polymeric materials, materials which are used to manufacture medical devices.

After the formation of the blood clots have occurred on the device surface, the clots could break off from the surface, travel through the blood stream, become lodged in a blood vessel and obstruct blood flow. Thrombosis is an especially major problem for permanently implanted devices that are in continuous blood contact.

A great deal of work has been done to develop coatings which reduce cell adhesion and activation. These coatings, referred to as biomimetic coatings, can inhibit the formation of blood clots and, therefore, reduce the possibility of thrombosis from occurring.

One such family of biomimetic coatings are surfactants described by Marchant et al. in U.S. Pat. Nos. 6,759,388 and 7,276,474 and U.S. patent application publications 20080247988 and 20080262614, which are herein incorporated by reference.

These coatings provide good blood clot inhibition. However, these coatings, which are adhered to many medical device surfaces, particularly those that are in constant contact with blood, could benefit from improved mechanical stability. In particular, these devices are often subjected to surface abrasion during handling prior to implantation, or while in use, which could remove the biomimetic coating from their surface. In addition, these coatings are often subjected to increased shear stresses during implantation that could lead to degradation of the coating over time. Degradation may include cracking, scratching, delamination, or spalling of the coating. Furthermore, such coatings may also be subject to dissolution in the body once implanted.

Therefore, there is a need to provide a means of modifying the biomimetic coating to improve its mechanical stability on the surface of a medical device surfaces. Specifically, a biomimetic coating with improved resistance to cracking, scratching, spalling, chemical dissolution and surface adhesion is provided.

SUMMARY OF THE INVENTION

The present invention relates to the modification of the chemical structure of a biomimetic coating that is applied to the surface of implantable medical devices. Specifically, the present invention describes various embodiments by which the chemical structure of a biomimetic surfactant is modified through incorporation of crosslinking agents. The incorporation of such crosslinking agents generally improves the mechanical stability of the surfactant coating, thus reducing its tendency to scratch or crack. Biomimetic surfactants, which will be discussed in more detail, are designed to reduce protein, platelet and leukocyte adhesion, and as a result, reduce the likelihood of thrombosis.

Biomimetic surfactants typically comprise a polymeric backbone of repeating monomeric units having functional groups for coupling with side chains. Generally, these surfactants comprise two main functional groups, a hydrophobic side chain functional group and a hydrophilic side chain functional group. The hydrophobic side chain affects the bonding adhesion of the surfactant to the substrate surface. The hydrophilic side chain functional group controls the biomimetic properties of the surfactant and creates an effective non-thrombogenic surface that retards blood clotting.

One such biomimetic surfactant polymer is poly(N-vinyl-dextran aldonamide-co-N-vinylhexanamide) and its related derivatives, developed by Marchant et al. This surfactant polymer is known to reduce platelet adhesion and activation on the coating surface, thereby reducing the likelihood of blood clotting and associated thrombosis that could result.

It is generally desirable for the biomimetic coating to be applied to the external surfaces of medical devices such as catheters, intravenous introducers, pacemakers, defibrillators, neurostimulators and their associated leads. The biomimetic coating inhibits blood clotting that results from blood contact with medical devices, particularly those that are implanted for long periods of time.

However, these coatings are generally prone to scratching, cracking or spalling that result from abrasion of the coating surface. Furthermore, such biomimetic coatings may dissolve from the surface of the medical device into the body over time. Such outcomes are not desirable since they could result in impairment and/or removal of the biomimetic coating from the surface of the medical device. If such an outcome were to occur, a patient could become increasingly vulnerable to the formation of a blood clot resulting from the damage or removal of the biomimetic coating.

Therefore, it is desirable to modify the chemical structure of the biomimetic surfactant coating to increase its mechanical stability. Increasing the mechanical stability of the surfactant thereby improves the coating's resistance to scratching, cracking and spalling due to abrasion, and the like. Furthermore, the increase in mechanical stability of the coating improves its long-term performance while implanted in the body.

The present invention does just that. It modifies the chemical structure of the biomimetic surfactant coating through the incorporation of a crosslinking agent, which binds two or more surfactant molecules together. The first embodiment modifies the chemical structure through the use of gluataldehyde to crosslink the hydrophilic dextran groups of the surfactant. In this embodiment, glutaraldehyde, chemical formula $(CH_2)_3$, is used as a crosslinking agent that bonds the dextran molecules together. Specifically, the hydroxyl groups of the dextran component are bonded to the aldehyde groups of the glutaraldehyde.

The second embodiment modifies the chemical structure of the biomimetic surfactant through incorporation of oxidized dextran. The oxidation of dextran converts a portion of the dextran hydroxyl groups to aldehyde groups. These aldehyde dextran groups are bonded to the hydroxyl groups of the dextran comprising the biomimetic surfactant, thereby crosslinking the surfactant molecules together. In this embodiment, the incorporation of the oxidized dextran as a crosslinking agent is similar to the use of glutaraldehyde, in that the aldehyde groups of the respective crosslinking agents bond to the hydroxyl dextran molecules of the biomimetic surfactant material.

The third embodiment modifies the chemical structure of the biomimetic surfactant through use of a cross-linkable hydrophobic functional group. The crosslinking hydrophobic functional group is incorporated within the polyvinylamine backbone of the surfactant material. In this embodiment, a fatty acid with a photoactive functional group such as (2E, 4E)-2,4-hexadienoic acid, 5-hexenoic acid, (3E)-3-hexenoic acid, or (2E)-3-phenyl-2-propenoic acid may be incorporated within the hydrocarbon backbone of the surfactant. Once the modified surfactant is applied to the surface of the substrate, UV light is applied to the surface of the modified surfactant to initiate crosslinking of the hydrophobic functional groups.

The term "hydrophobic" is defined herein as repelling, tending not to combine with, or incapable of dissolving in water. The term "biomimetic" is defined herein as mimicking bodily cell interaction at the molecular level so as not to cause an adverse affect or reaction in the body. The term "non-thrombogenic" is defined herein as prohibiting the coagulation of blood from occurring in a blood vessel. The term "mechanical stability" is herein defined as a resistance to delamination, abrasion, scratching, spalling or cracking. The term "substrate" is defined herein as a base material, which can be modified through the application of a surface coating or through the incorporation of dopant materials during processing of the base material. As referred to in this present invention, a substrate surface refers to the surface of a medical device.

DETAILED DESCRIPTION OF THE PREFERRED EMBODIMENTS

Figure 1:
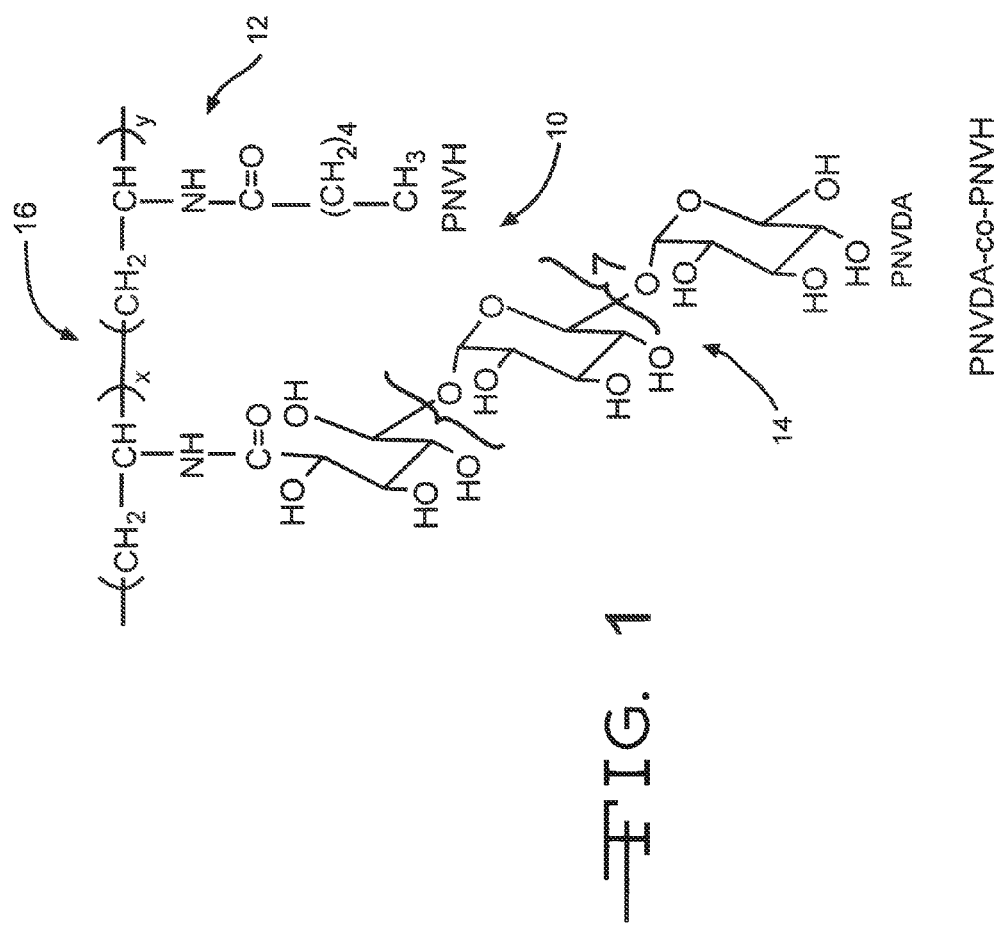
FIG. 1 is a depiction showing the chemical structure of an embodiment of a biomimetic surfactant used in the present invention.

In the present invention, the chemical structure of a biomimetic surfactant, namely, poly(N-vinyldextran aldonamide-co-N-vinylhexanamide), is modified to improve its mechanical stability and adhesion to the surface of a medical device. As shown in FIG. 1, the biomimetic surfactant comprises a chemical structure 10 that is composed of a combination of a hydrophobic molecular chain and a hydrophilic molecular chain. The hydrophobic molecular chain comprises a poly(N-vinyl hexanoyloxy)(PNVH) component 12 and the hydrophilic molecular chain comprises a poly(N-vinyl dextran aldonamide)(PNVDA) component 14. The molecular weight of the preferred surfactant ranges from about 1,000 to about 2,000,000 dalton.

As illustrated in FIG. 1, the preferred biomimetic surfactant has a comb-like structure that comprises a flexible polymeric backbone 16 that is linked to a combination of a plurality of hydrophobic side chains, poly(N-vinyl hexanoamide) (PNVH) 12 and a plurality of hydrophilic side chains, poly(N-vinyl dextran aldonamide) (PNVDA), 14. In a preferred embodiment, the polymeric backbone 16 comprises polyvinylamine (PVAm).

The hydrophobic side chains 12 comprise alkyl groups that are linked to the polymeric backbone 16 via an ester linkage, an amine linkage or an amide linkage. Preferably, the hydrophobic chains 12 are attached to the polymeric backbone 16 by reacting an alkanoyl $(CH_3(-CH_2-)_nCO-)$ or an alkanal $(CH_3(CH_2-)_nCHO)$ with the homopolymer of the backbone.

To form a coating which blocks adhesion of non-specific plasma proteins on the surface of the substrate, the surfactant polymer preferably comprises a plurality of hydrophilic side chains formed from oligosaccharides with an average molecular weight of less than 7,000 dalton. Such surfactant polymers may be ionic or non-ionic and are not limited to natural oligosaccharides, such as dextran. The hydrophilic side chains 14 are linked to the polymeric backbone 16 through an ester linkage, a secondary amine linkage or preferably an amide linkage.

Alternatively, a charged oligosaccharide, preferably of a negatively charged oligosaccharide having an average molecular weight less than 10,000 dalton, and an oligopeptide containing about 3 to about 30 amino acid residues of the oligopeptide may also be used. The amino acid sequence of the oligopeptide interacts with protein receptors on the surface of the cells such as endothelial cells.

Alternate biomimetic surfactants comprising poly(N-vinyl dextran aldonamide-co-N-vinyl dodecanoamide)(PNVDA-co-PNVL), poly(N-vinyl hexyl amine-co-N-vinyl heparinamine)(PNVHA-co-PNVHep A), poly(N-vinyl hexyl amine-co-N-vinyl heparinamine-co-N-vinyl maltonoamide) (PNVHA-co-PN-VHepA-co-PNVM), and poly(N-vinyl-5-peptidyl-pentylamine-co-N-vinyl-dextranaldonamine-co-N-vinyl hexyl amine (PVAm(Pep:Dex:Hex)) may also be used.

The modified biomimetic surfactants of the present invention are preferably applied to a polymeric material, more preferably comprising silicone, polyurethane or a polyether block amide. It is further preferred that the modified biomimetic surfactants of the present invention be applied to the surface of such medical devices as pacemakers, defibrillators, neurostimulators, introducers, leads, catheters and stents.

In general, two modes of crosslinking surfactant molecules are described. In the first mode, the neighboring molecules of the surfactant polymer are bonded together through the linking of the hydrophilic side chains 14. In this mode, aldehyde groups, chemical formula, (CHO), of a hydrophilic crosslinking agent are bonded together with the hydroxyl groups, chemical formula —OH, of the dextran component of the hydrophilic side chains 14 of the biomimetic surfactant 10.

In the second mode, neighboring molecules of the surfactant polymer are bonded together through linking of modified hydrophobic side chains 12 comprising the surfactant. In this second mode, a photoactive fatty acid constituent, such as (2E,4E)-2,4-hexadienoic acid, is incorporated within the polyvinylamine backbone 16 of the surfactant replacing the hexanoic acid as the hydrophobic component 12 of the surfactant.

Figure 2:
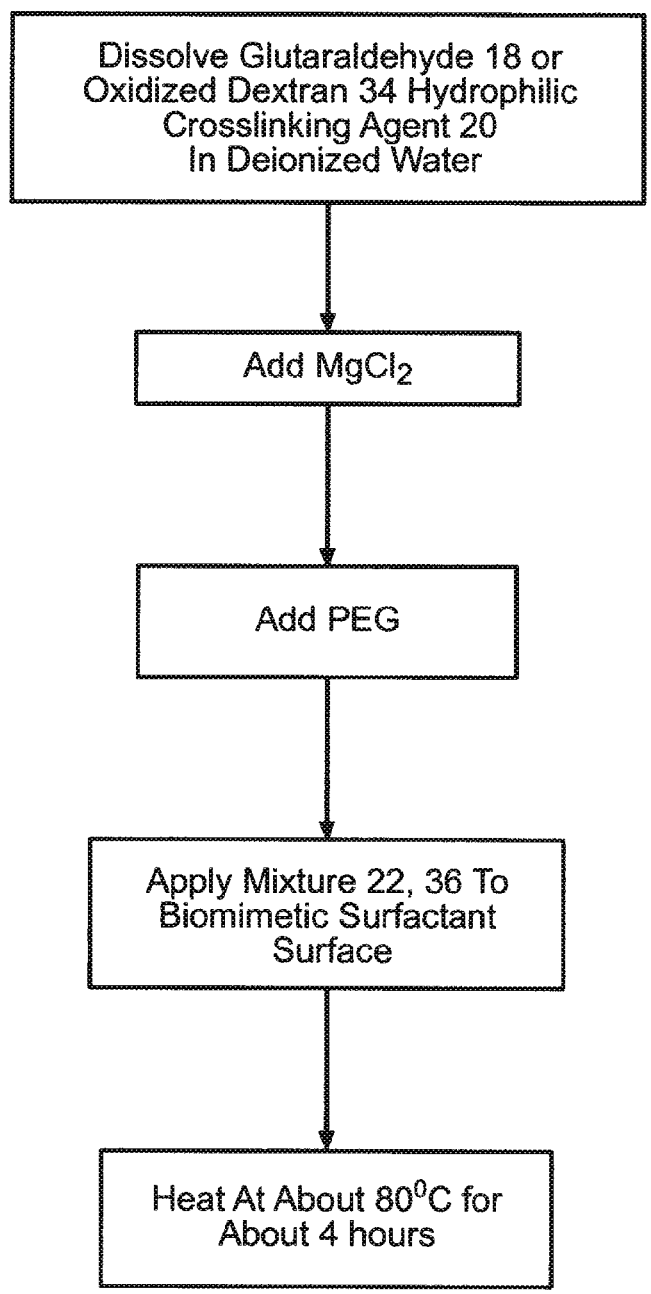
FIG. 2 is a flow chart depicting an embodiment of a procedure used to fabricate a hydrophilic crosslinking mixture of the present invention.

In reference to the first mode, crosslinking of hydrophilic side chains 14, the chemical structure of the surfactants can be modified in either of two preferred embodiments. As depicted in FIG. 2, the first preferred embodiment utilizes a glutaraldehyde constituent 18, chemical formula $(CH_2)_3$, as a hydrophilic cross linking agent 20 within the surfactant material. In this embodiment, a hydrophilic crosslinking mixture 22 comprising glutaraldehyde (GA), polyethylene glycol (PEG), $MgCl_2$, and deionized water is first prepared. The glutaraldehyde (GA) acts as the crosslinking agent, the polyethylene glycol (PEG) acts as a plasticizer and the $MgCl_2$ acts as the catalyst for the crosslinking reaction. Preferably, this hydrophilic crosslinking mixture 22 comprises about 10 to about 50 weight percent glutaraldehyde (GA), about 1 to about 10 weight percent $MgCl_2$, about 1 to about 20 weight percent PEG, more preferably PEG400, the remainder comprising deionized water. An exemplary embodiment of the glutaraldehyde hydrophilic crosslinking mixture 22 comprises about 35 weight percent glutaraldehyde (GA), about 6 weight percent PEG400, about 5 weight percent $MgCl_2$, and about 54 weight percent deionized water.

The hydrophilic crosslinking mixture 22 is prepared by first dissolving the glutaraldehyde (GA) constituent 18 in deionized water. Once dissolved, the $MgCl_2$ and PEG constituents are then added to the mixture. A flow chart illustrating the preferred procedure of preparing the glutaraldehyde (GA) hydrophilic mixture 22 is given in FIG. 2. After the crosslinking mixture 22 is prepared, it is applied to the surface of the biomimetic surfactant 10, such as poly(N-vinyldextran aldonamide-co-N-vinylhexanamide), as discussed earlier.

Figure 3:
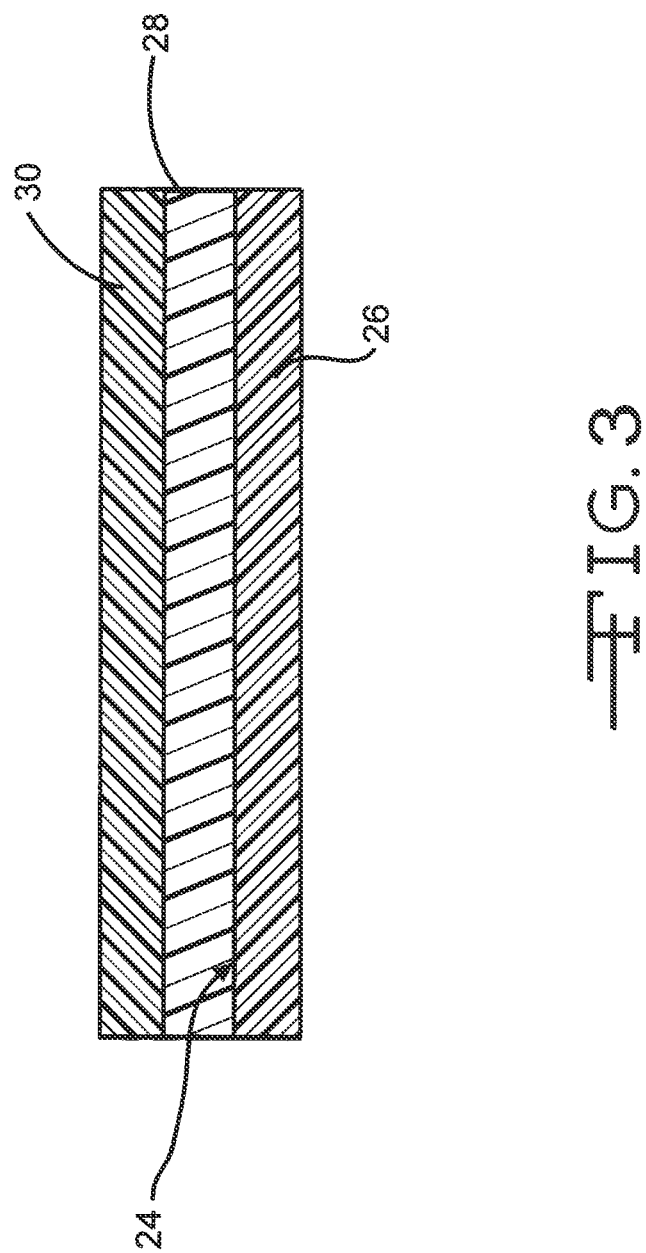
FIG. 3 is a cross-sectional view showing an embodiment of first layer of biomimetic surfactant and a second layer of hydrophilic crosslinking mixture on a substrate surface.

In a preferred embodiment, the biomimetic surfactant coating 10 is first prepared and applied to a surface 24 of a substrate 26. Examples of the preparation of this biomimetic surfactant and application to the surface 24 of the substrate 26 are given in U.S. patent application Ser. No. 12/062,768 (U.S. patent application Pub. No. 20080262614), to Marchant et al, which is incorporated herein. FIG. 3 illustrates a cross-sectional view of the initial application of the layers of surfactant coating and hydrophilic crosslinking mixture. As FIG. 3 shows, a first layer 28 of biomimetic surfactant 10 is applied to the surface 24 of the substrate 26 and a second layer 30, comprising the hydrophilic crosslinking mixture 22 is applied to the surface of the first layer 28 of the surfactant coating. It should be noted that multiple layers of either the surfactant 10 and/or the hydrophilic crosslinking mixture 22 may be applied. It is further contemplated that these layers 28, 30 of surfactant 10 and hydrophilic crosslinking mixture 22 may be positioned such that they are alternating.

A preferred method of applying the hydrophilic crosslinking mixture 22 is by dip coating the mixture 22 onto the surface of the first layer 28 of biomimetic surfactant 10. Although dip coating is the preferred method of applying the crosslinking mixture 22, a multitude of non-limiting techniques such as spray coating, gas plasma deposition, chemical vapor deposition, physical deposition process, spin coating or brush application may also be used.

Once the hydrophilic cross linking mixture 22 is applied to the surface of the biomimetic surfactant, the crosslinking mixture 22 is dried using lyophilization at room temperature until all water is removed. The coating is then cured at a temperature ranging from about 60° C. to about 100° C. for about 2 to about 6 hours in an ambient atmosphere. More preferably, the crosslinking mixture 22 is cured at about 80° C. for about 4 hours.

Figure 4:
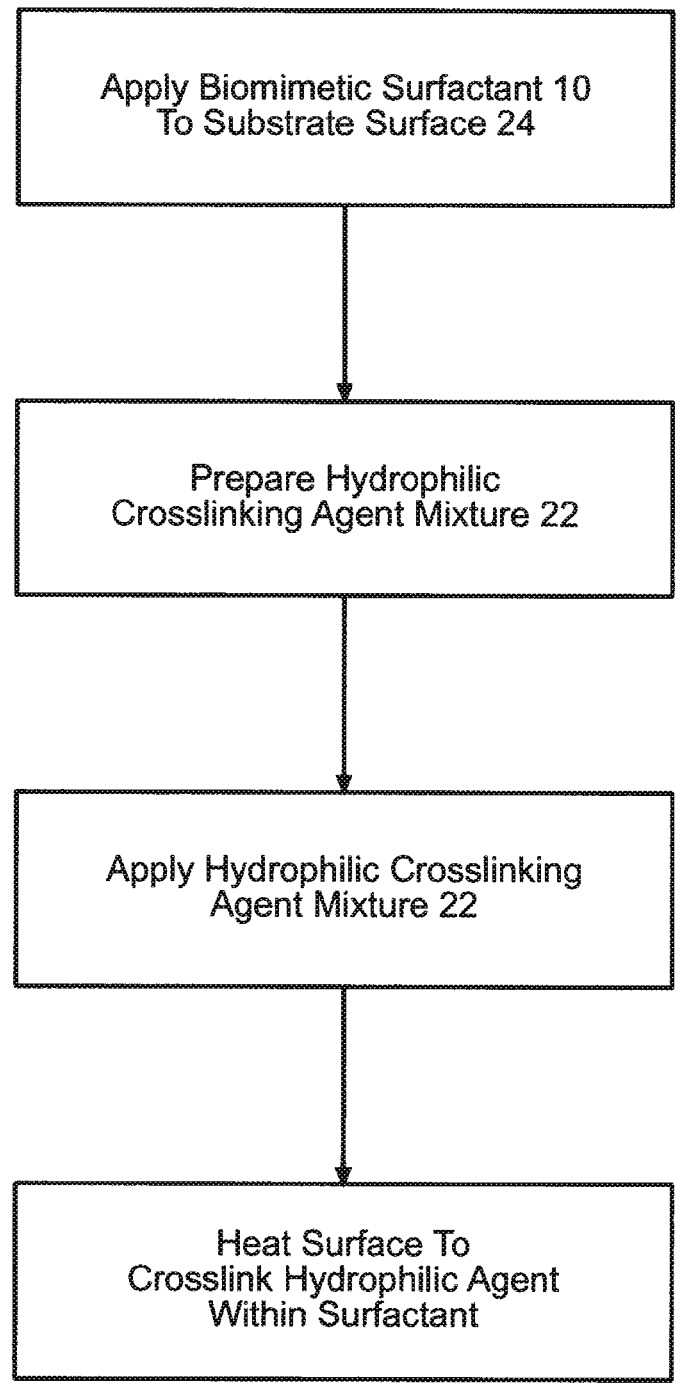
FIG. 4 is a flow chart illustrating the sequence in modifying the biomimetic surface with a hydrophilic crosslinking agent.

FIG. 4 illustrates a flow chart of the preferred process of incorporating the hydrophilic crosslinking agent within the surfactant. After curing, the surface of the resulting hydrophilic crosslinked surfactant is rinsed with deionized water to remove any particles of surface contamination. The curing process diffuses the crosslinking mixture 22 into the surfactant material resulting in the incorporation of the glutaraldehyde (GA) constituent 18 within the chemical structure of the resultant surfactant.

Figure 5:
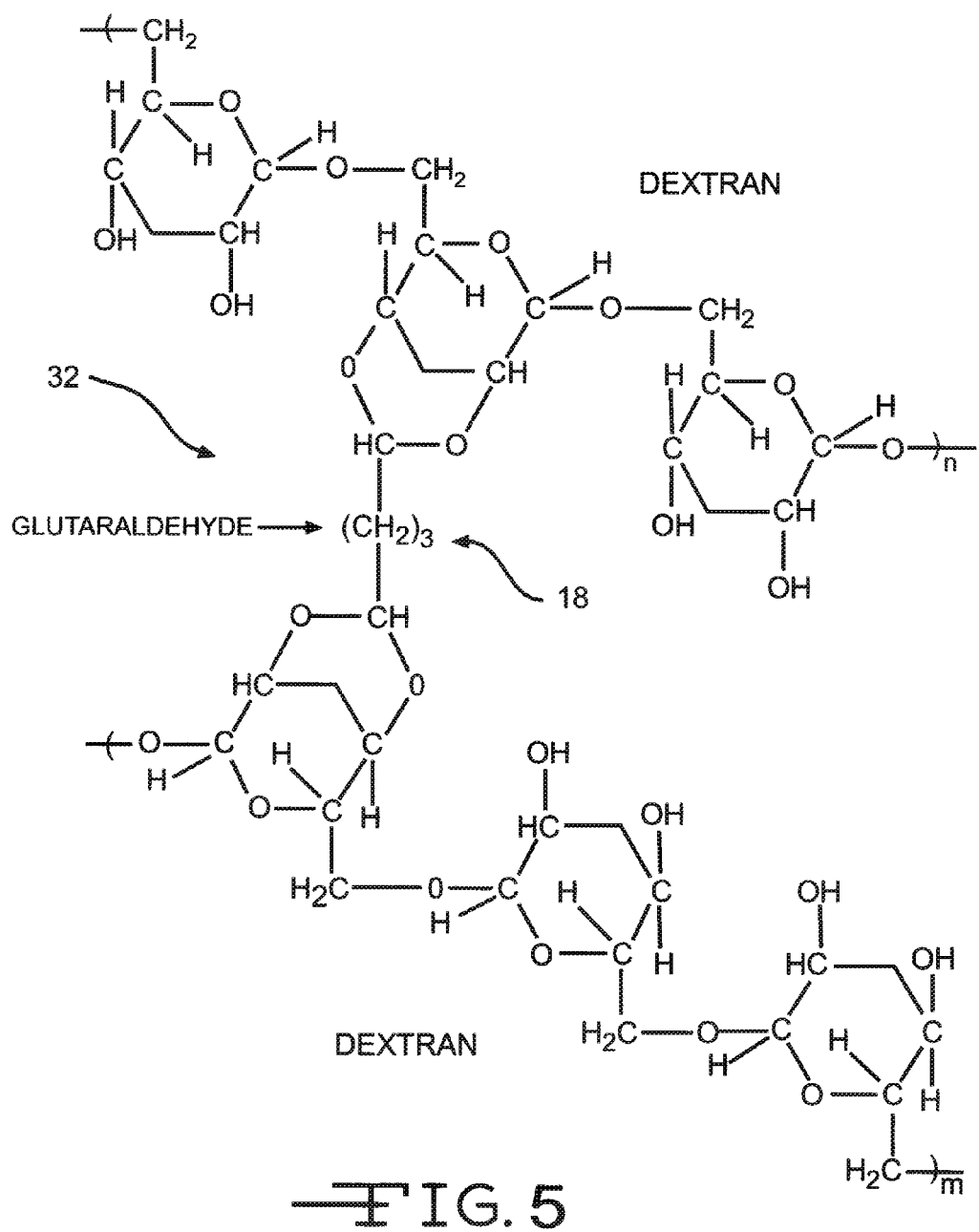
FIG. 5 is an illustration of the chemical structure of an embodiment of a glutaraldehyde hydrophilic crosslink modified surfactant.

FIG. 5 illustrates the chemical structure of a glutaraldehyde modified surfactant 32 of the present invention. As illustrated, the aldehyde groups (CHO) of the glutaraldehyde constituent 18, is bonded with the hydroxyl group (—OH) of the dextran component of the surfactant coating, thereby linking the dextran components together.

In a second preferred embodiment, an oxidized dextran constituent 34 is used as the hydrophilic crosslinking agent 20. In this second preferred embodiment, the oxidized dextran 34 replaces the glutaraldehyde (GA) constituent 18 as embodied in the first embodiment, previously described.

In the second preferred embodiment, an oxidized dextran hydrophilic crosslinking mixture 36 comprising oxidized dextran, polyethylene glycol (PEG), preferably PEG400, $MgCl_2$ and deionized water is prepared. The oxidized dextran 34 acts as the crosslinking agent 20, the polyethylene glycol (PEG) acts as a plasticizer and the $MgCl_2$ acts as a catalyst for the crosslinking reaction.

In general, on a per weight basis, oxidized dextran 34 comprises a greater number of aldehyde groups as compared to glutaraldehyde (GA) 18. Therefore, the increased number of aldehyde groups of the oxidized dextran provides more sites with which to bond and crosslink the hydroxyl groups of the dextran constituent of the surfactant body. This allows a more effective means of controlling the degree of crosslinking. For example, increasing the amount of oxidized dextran will generally increase the degree of crosslinking, which translates to an increase in mechanical stability. In addition, a wide range of molecular weight dextran may be utilized as the crosslinking agent. The molecular weight of the oxidized dextran can range from about 1,500 dalton to about 200,000 dalton. It is generally understood that incorporating a higher molecular weight dextran also improves the mechanical stability of the biomimetic surfactant coating. Therefore, by altering the molecular weight of the oxidized dextran constituent, the mechanical stability of the resulting biomimetic surfactant coating can be modified to specific application requirements.

The dextran constituent may be oxidized using a variety of methods. In one embodiment, dextran is oxidized using sodium metaperiodate, chemical formula $Na_2H_3IO_6$. In this embodiment, dextran is oxidized by mixing the dextran in solution with sodium metaperiodate and deionized water. In a preferred embodiment, a dextran intermediary solution 38 is prepared by dissolving dextran in deionized water in a ratio of about 5-15 g dextran to about 100 ml of deionized water. A separate sodium metaperiodate intermediary solution 40 is prepared by dissolving sodium metaperiodate in deionized water in a ratio of about 3 g to about 12 g sodium metaperiodate to about 100 ml of deionized water. Alternatively, periodic acid ($HIO_4$) may be substituted for the sodium metaperiodate.

Figure 6:
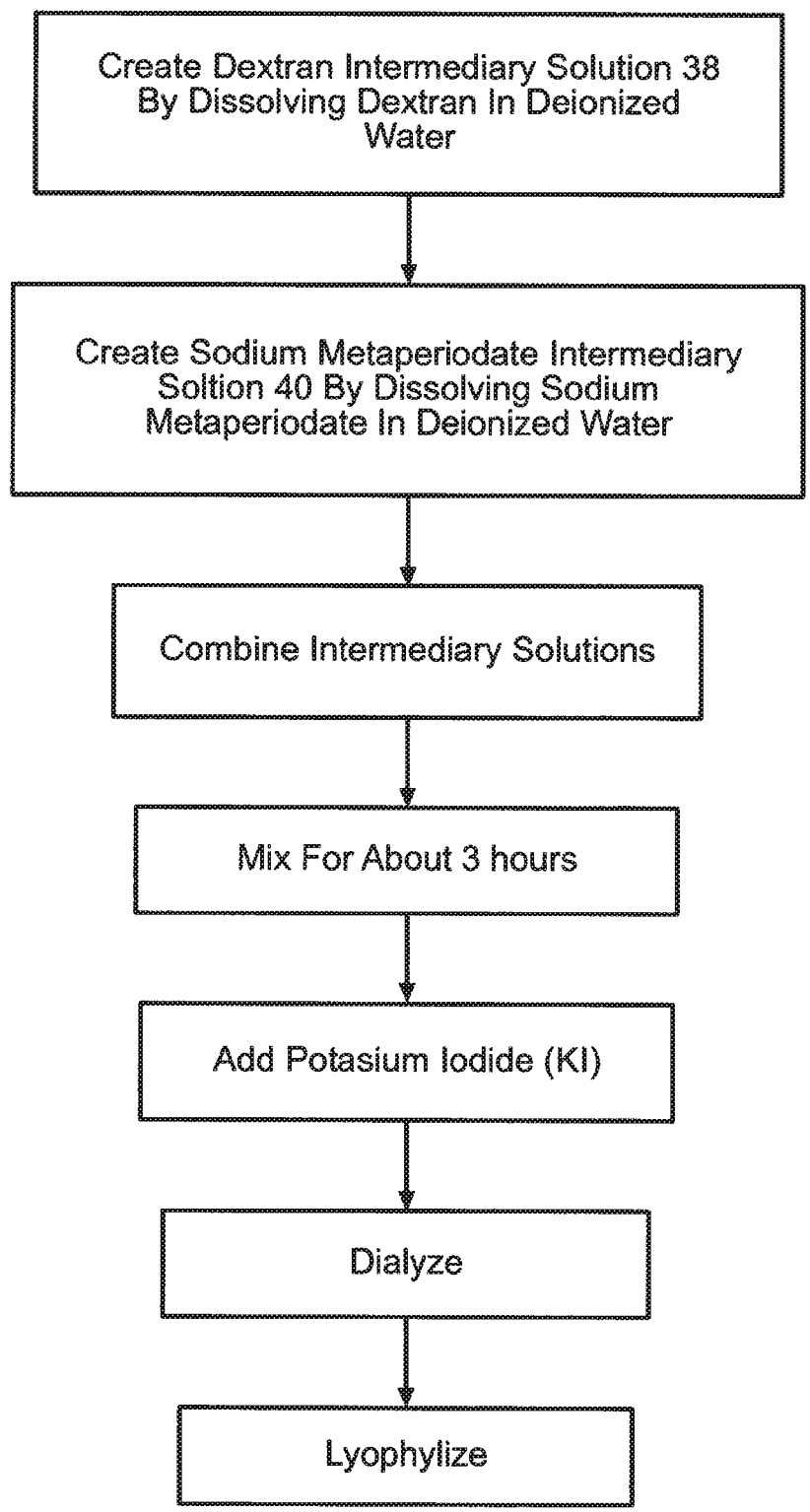
FIG. 6 shows a flow chart illustrating the sequence of an embodiment of preparing oxidized dextran.

These two intermediary solutions 38, 40 are then mixed together at room temperature for about 3 hours, preferably in, an area that is devoid of light. After the two intermediary solutions are mixed, potassium iodide (KI) is added to the mixture. In a preferred embodiment, about 20 mL of 4.5M potassium iodide is added to the mixture. The combined mixture is dialyzed against deionized water at room temperature and dried using lyophilization at room temperature until a substantial amount of water is removed. FIG. 6 illustrates a flow chart of the preferred dextran oxidation process.

The resulting oxidized dextran constituent 34 is then mixed with polyethylene glycol (PEG), $MgCl_2$, and deionized water to create the oxidized dextran crosslinking mixture 36. In a preferred embodiment, the oxidized dextran crosslinking mixture 36 comprises from about 10 to about 50 weight percent oxidized dextran, having a molecular weight ranging from about 1,000 dalton to about 80,000 dalton, about 1 weight percent to about 10 weight percent $MgCl_2$, about 1 weight percent to about 20 weight percent PEG, more preferably PEG400, and the remainder comprising deionized water.

Similar to the glutaraldehyde crosslinking mixture 22 previously discussed, the oxidized dextran crosslinking mixture 36 is preferably applied directly to the surface of the surfactant 10. In a preferred embodiment, the oxidized dextran crosslinking mixture 36 is applied through dip coating the mixture onto the surface of the biomimetic coating as illustrated in FIG. 2. Although dip coating is the preferred method of applying the crosslinking mixture 36, a multitude of non-limiting techniques including spray coating, gas plasma deposition, chemical vapor deposition, physical deposition process, spin coating or brush application may also be used.

Figure 7:
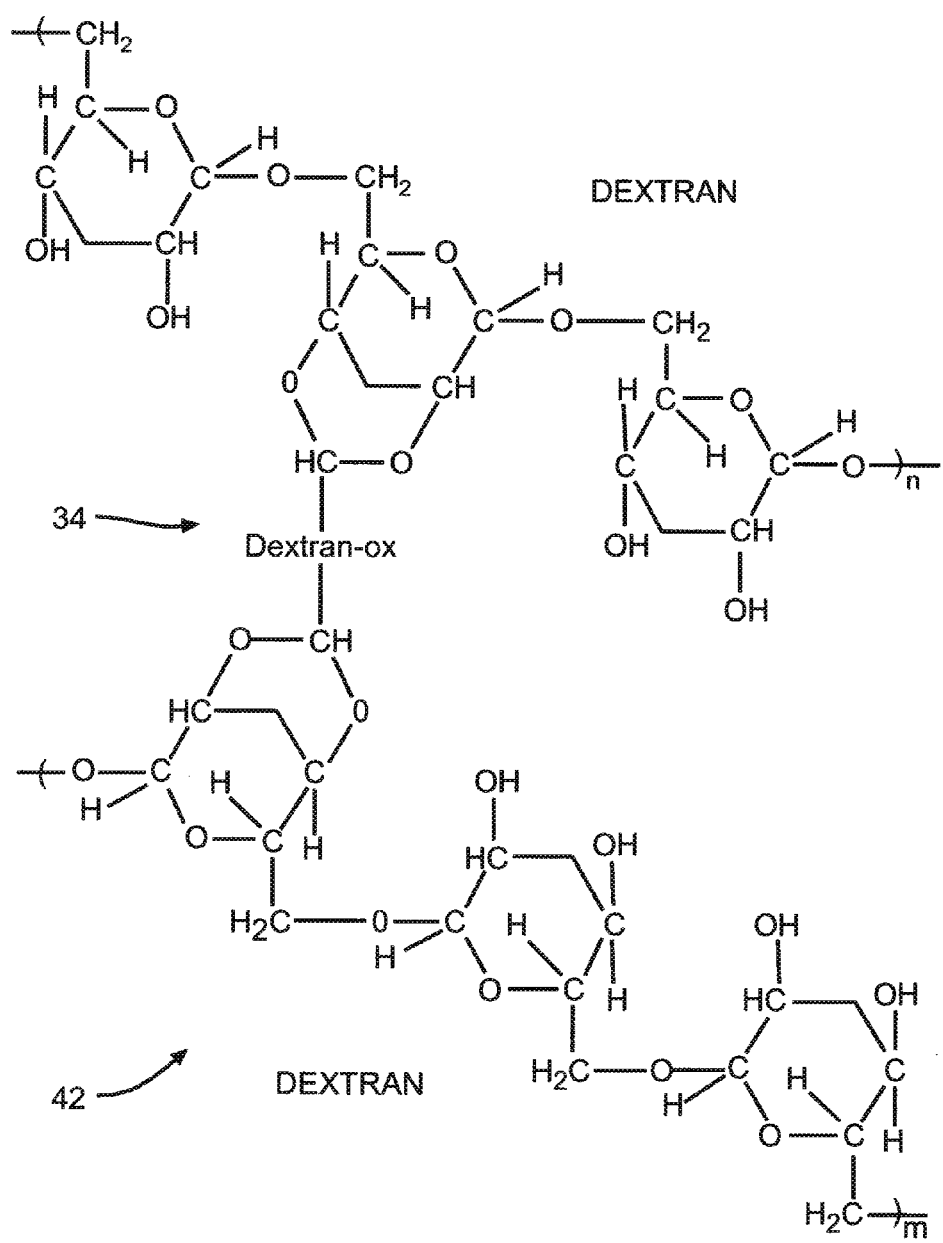
FIG. 7 is an illustration of the chemical structure of an embodiment of an oxidized dextran hydrophilic crosslink modified surfactant.

Also similar to the glutaraldehyde crosslinking embodiment, once the oxidized dextran cross linking mixture 36 is applied to the surface of the biomimetic coating 10, the crosslinking mixture 36 is dried and heat cured. In a preferred embodiment, the mixture is dried using lyophilization until a substantial amount of water is removed and then cured at a temperature ranging from about 60° C. to about 100° C. for about 2 to about 6 hours in an ambient atmosphere. More preferably, the crosslinking mixture 36 is cured at about 80° C. for about 4 hours. After curing, the chemical structure of the surfactant 10 becomes modified to an oxidized detran crosslinked surfactant 42. The curing process diffuses the oxidized dextran 34 into the structure of the surfactant 42 and activates crosslinking of the molecules therebetween. This modified surfactant 42 is rinsed with deionized water to remove any particles of surface contamination. FIG. 7 illustrates the chemical structure of the oxidized dextran surfactant 42. As shown, the oxidized dextran 34 is crosslinked to the hydroxyl groups of the dextran constituent of the surfactant body.

Figure 8A:
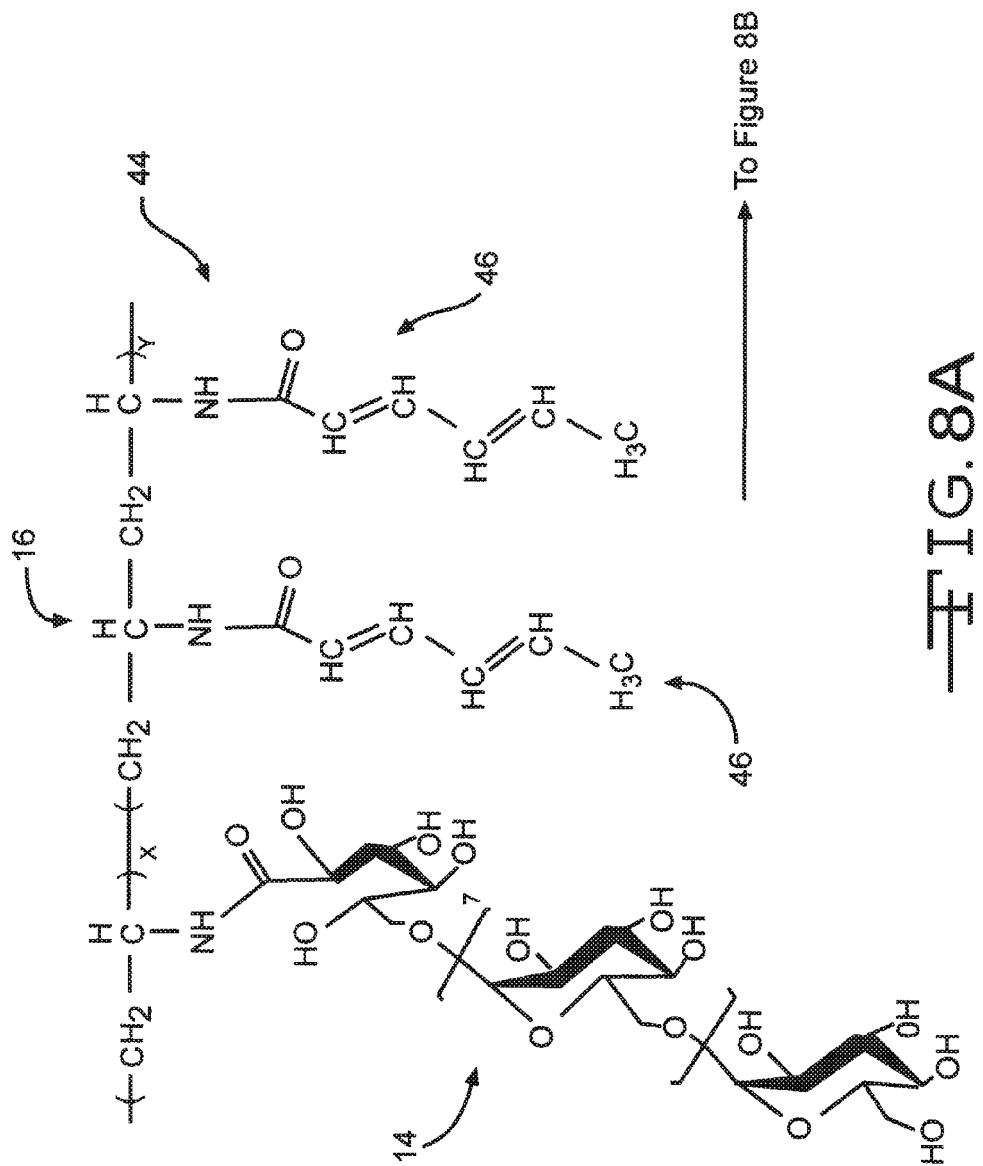
FIG. 8A illustrates the chemical structure of an embodiment of a UV crosslinkable surfactant polymer prior to UV light exposure.
Figure 8B:
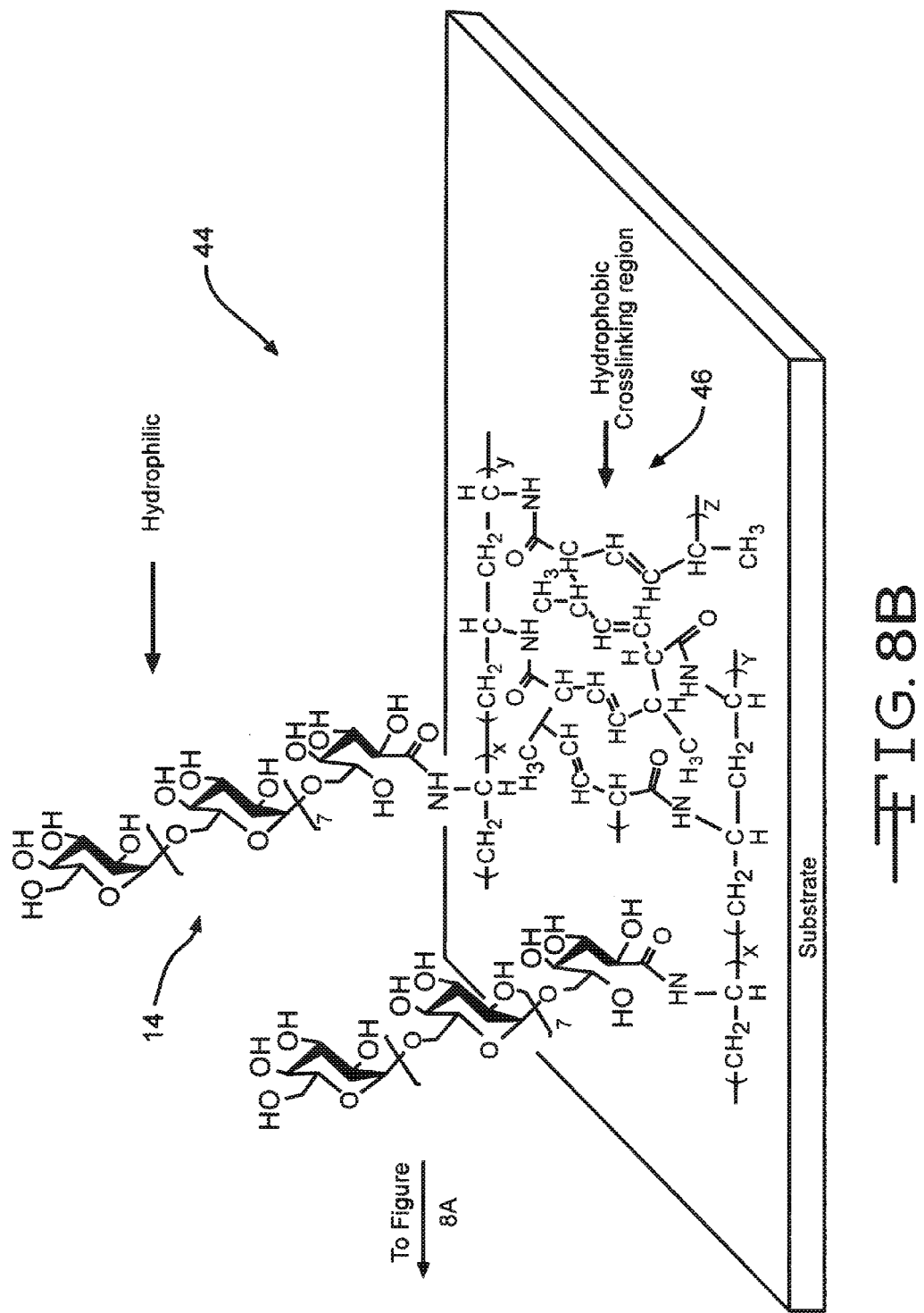
FIG. 8B illustrates the chemical structure of an embodiment of a UV crosslinked surfactant polymer post UV light exposure.

In a third mode, a UV photo activated biomimetic surfactant 44 is fabricated. In this embodiment, a "photo-crosslinkable" hydrophobic functional group 46 is incorporated within the polyvinylamine backbone 16 during formulation of the surfactant 44. As a result, the UV crosslinkable surfactant polymer 44 is created without the need to diffuse a crosslinking agent within the chemical structure post surfactant fabrication. The chemical structure of the UV photo activated surfactant 44 is shown in FIGS. 8A and 8B.

Unlike the prior embodiments, in which the surfactant 10 is modified through application of a hydrophilic crosslinking agent that is incorporated within the chemical structure of the surfactant through diffusion and heat treatment, the UV photo activated biomimetic surfactant 44 is formulated with the "photo-crosslinkable" hydrophobic functional group 46. The modified UV activated surfactant polymer 44 is directly applied to the surface of the substrate 26, such as a surface of a medical device, without the addition of a crosslinking mixture. The "photo-crosslinkable" hydrophobic functional group 46 is activated when ultra violet light is shown on the surface of the modified surfactant 44.

In a preferred embodiment, the "photo-crosslinkable" hydrophobic functional group 46 comprises a fatty acid. More specifically, the "photo-crosslinkable" hydrophobic functional group 46 comprises a hydrophobic fatty acid with photoactive functional groups, such as (2E,4E)-2,4-hexadienoic acid, 5-Hexenoic acid, (3E)-3-hexenoic acid, or (2E)-3-phenyl-2-propenoic acid.

In addition to the "photo-crosslinkable" hydrophobic functional group 46, the surfactant 44 comprises a hydrophilic functional group side chain 14. The hydrophilic functional group side chain 14 may comprise poly(N-vinyl dextran aldonamide) (PNVDA). The UV activated hydrophobic fatty acid functional group 46 is chemically attached to the polymeric backbone 16 such as polyvinylamine (PVAm) of the surfactant 44, as shown in FIG. 8A. In a preferred embodiment, the hydrophobic UV photo active functional group 46 replaces the poly(N-vinyl hexanoyloxy)(PNVH) hydrophobic functional group component 12 of the surfactant 10.

Once the modified surfactant polymer 44 is applied to the surface of the substrate, i.e., a surface of a medical device, UV light is applied to the surface of the surfactant 44 to activate crosslinking therewithin. Specifically, the UV light activates crosslinking of the photoactive fatty acid functional groups 46 within the hydrophobic chain 12 of the surfactant 44. FIG. 8B illustrates the chemical structure of this UV light modified surfactant polymer after exposure to UV light. As shown in a preferred embodiment, the UV activated hydrophobic functional group 46 is bonded between polymeric backbones 16 comprising the surfactant 44.

It is appreciated that various modifications to the invention concepts described herein may be apparent to those skilled in the art without departing from the spirit and the scope of the present invention defined by the hereinafter appended claims.

What is claimed is:

1. A surfactant polymer modified with a crosslinking agent, the modified surfactant polymer comprising:
   a) at least one polymeric backbone chemically bonded to at least one hydrophilic molecular chain and at least one hydrophobic molecular chain, wherein either the hydrophilic molecular chain or the hydrophobic molecular chain comprises a hydroxyl functional group;
   b) a crosslinking agent comprising an aldehyde functional group therewithin; and
   c) wherein the aldehyde functional group of the crosslinking agent is chemically bonded with the hydroxyl functional group within the surfactant polymer.

2. The surfactant polymer of claim 1 wherein the crosslinking agent comprises glutaraldehyde.

3. The surfactant polymer of claim 2 wherein the glutaraldehyde is a component of a crosslinking mixture comprising about 10 to about 50 weight percent glutaraldehyde about 1 to about 10 weight percent MgCl$_2$, about 1 to about 20 weight percent polyethylene glycol, the remainder comprising deionized water that is chemically incorporatable with the surfactant polymer.

4. The surfactant polymer of claim 1 wherein the crosslinking agent comprises oxidized dextran.

5. The surfactant polymer of claim 4 wherein the oxidized dextran is a component of a crosslinking mixture comprising from about 10 to about 50 weight percent oxidized dextran, from about 1 to about 10 weight percent MgCl$_2$, from about 1 to about 20 weight percent polyethylene glycol, the remainder comprising deionized water that is chemically incorporatable with the surfactant polymer.

6. The surfactant polymer of claim 1 wherein the polymeric backbone comprises polyvinylamine.

7. The surfactant polymer of claim 1 wherein the at least one hydrophilic molecular chain comprises poly(N-vinyl dextran aldonamide).

8. The surfactant polymer of claim 1 wherein the aldehyde functional group within the crosslinking agent chemically bonds with the hydroxyl functional group within a dextran constituent of the hydrophilic molecular chain.

9. The surfactant polymer of claim 1 wherein the surfactant is adhereable to a surface of a medical device selected from the group consisting of a pacemaker, a defibrillator, a neurostimulator, a venous introducer, a catheter, a lead, and a stent.

10. The surfactant polymer of claim 1 wherein the surfactant polymer is selected from the group consisting of poly(N-vinyldextran aldonamide-co-N-vinylhexanamide), poly(N-vinyl dextran aldonamide-co-N-vinyl dodecanoamide) (PNVDA-co-PNVL), poly(N-vinyl hexyl amine-co-N-vinyl heparinamine)(PNVHA-co-PNVHepA), poly(N-vinyl hexyl amine-co-N-vinyl heparinamine-co-N-vinyl maltonoamide) (PNVHA-co-PN-VHepA-co-PNVM), and poly(N-vinyl-5-peptidyl-pentylamine-co-N-vinyl-dextranaldonamine-co-N-vinyl hexyl amine (PVAm(Pep:Dex:Hex)).

11. The surfactant polymer of claim 1 wherein the crosslinking agent comprises a molecular weight ranging from about 1,500 dalton to about 200,000 dalton.

12. A method of modifying a surfactant polymer, the method comprising:
a) providing a surfactant polymer comprising:
i) at least one polymeric backbone;
ii) at least one hydrophilic molecular chain chemically bonded to the at least one polymeric backbone;
iii) at least one hydrophobic molecular chain chemically bonded to the at least one polymeric backbone; and
iv) wherein either the hydrophilic molecular chain or the hydrophobic molecular chain comprises a hydroxyl functional group;
b) providing a crosslinking mixture comprising at least one aldehyde functional group;
c) applying a layer of the surfactant polymer to a first surface;
d) applying a layer of the crosslinking mixture to a second surface of the surfactant polymer; and
e) heating the layer of surfactant polymer and layer of crosslinking mixture so that the aldehyde functional group of the crosslinking mixture chemically bonds with the hydroxyl functional group within the surfactant polymer.

13. The method of claim 12 including selecting the surfactant polymer from the group consisting of poly(N-vinyldextran aldonamide-co-N-vinylhexanamide), poly(N-vinyl dextran aldonamide-co-N-vinyl dodecanoamide)(PNVDA-co-PNVL), poly(N-vinyl hexyl amine-co-N-vinyl heparinamine)(PNVHA-co-PNVHepA), poly(N-vinyl hexyl amine-co-N-vinyl heparinamine-co-N-vinyl maltonoamide) (PNVHA-co-PN-VHepA-co-PNVM), and poly(N-vinyl-5-peptidyl-pentylamine-co-N-vinyl-dextranaldonamine-co-N-vinyl hexyl amine (PVAm(Pep:Dex:Hex)).

14. The method of claim 12 further providing the crosslinking mixture comprising about 10 to about 50 weight percent glutaraldehyde, about 1 to about 10 weight percent MgCl$_2$, about 1 to about 20 weight percent polyethylene glycol, the remainder comprising deionized water.

15. The method of claim 12 further providing the crosslinking mixture comprising about 10 to about 50 weight percent oxidized dextran, about 1 to about 10 weight percent MgCl$_2$, about 1 to about 20 weight percent polyethylene glycol, the remainder comprising deionized water.

16. The method of claim 12 further heating the layer of surfactant polymer and the layer of crosslinking mixture at a temperature ranging from about 60° C. to about 100° C. for about 2 to about 6 hours in an ambient atmosphere.

17. The method of claim 12 further providing the step of applying the layer of surfactant polymer to a surface of a medical device selected from the group consisting of a pacemaker, a defibrillator, a neurostimulator, a venous introducer, a catheter, a lead, and a stent.

18. The method of claim 12 including providing the dextran comprising a molecular weight ranging from about 1,500 dalton to about 200,000 dalton.

19. The method of claim 12 including providing the oxidized dextran comprising sodium metaperiodate.

20. A surfactant polymer modified with a crosslinking agent, the modified surfactant polymer comprising:
a) at least one polymeric backbone chemically bonded to at least one hydrophilic molecular chain and at least one hydrophobic molecular chain, wherein the hydrophilic molecular chain comprises a hydrophilic functional group;
b) a crosslinking agent comprising oxidized dextran; and
c) wherein the oxidized dextran is chemically bonded with the hydrophilic functional group within the surfactant polymer.

21. The surfactant polymer of claim 20 wherein the oxidized dextran is a component of a crosslinking mixture comprising from about 10 to about 50 weight percent oxidized dextran, from about 1 to about 10 weight percent MgCl$_2$, from about 1 to about 20 weight percent polyethylene glycol, the remainder comprising deionized water that is chemically incorporatable within the surfactant polymer.

22. The surfactant polymer of claim 20 wherein the polymeric backbone comprises polyvinylamine.

23. The surfactant polymer of claim 20 wherein the hydrophilic molecular chain comprises poly(N-vinyl dextran aldonamide).

24. The surfactant polymer of claim 20 wherein the oxidized dextran of the crosslinking agent comprises an aldehyde functional group, and wherein the aldehyde functional group is chemically bonded with the hydrophilic functional croup within the surfactant polymer.

25. The surfactant polymer of claim 20 wherein the at least one hydrophilic molecular chain comprises a hydroxyl functional group, and wherein the hydroxyl functional group is chemically bonded with the oxidized dextran within the crosslinking agent.

26. The surfactant polymer of claim 20 wherein the surfactant polymer is adhereable to a surface of a medical device selected from the group consisting of a pacemaker, a defibrillator, a neurostimulator, a venous introducer, a catheter, a lead, and a stent.

27. The surfactant polymer of claim 20 wherein the polymer is selected from the group consisting of poly(N-vinyl-dextran aldonamide-co-N-vinylhexanamide), poly(N-vinyl dextran aldonamide-co-N-vinyl dodecanoamide)(PNVDA-co-PNVL), poly(N-vinyl hexyl amine-co-N-vinyl heparinamine)(PNVHA-co-PNVHep A), poly(N-vinyl hexyl amine-co-N-vinyl heparinamine-co-N-vinyl maltonoamide)(PNVHA-co-PN-VHepA-co-PNVM), and poly(N-vinyl-5-peptidyl-pentylamine-co-N-vinyl-dextranaldonamine-co-N-vinyl hexyl amine (PVAm(Pep:Dex:Hex)).

28. The surfactant polymer of claim 20 wherein the oxidized dextran comprises a molecular weight ranging from about 1,500 dalton to about 200,000 dalton.

29. The surfactant polymer of claim 20 wherein the oxidized dextran comprises sodium metaperiodate.

* * * * *

UNITED STATES PATENT AND TRADEMARK OFFICE
CERTIFICATE OF CORRECTION

| | | |
|---|---|---|
| PATENT NO. | : 8,945,664 B1 | Page 1 of 1 |
| APPLICATION NO. | : 13/283763 | |
| DATED | : February 3, 2015 | |
| INVENTOR(S) | : Jan J. Lewandowski et al. | |

It is certified that error appears in the above-identified patent and that said Letters Patent is hereby corrected as shown below:

In the Claims

Column 10, line 25 (Claim 18, line 1) after the word "the" insert --oxidized--

Signed and Sealed this
Twelfth Day of May, 2015

Michelle K. Lee
*Director of the United States Patent and Trademark Office*